United States Patent
Meyer et al.

(10) Patent No.: US 10,093,734 B2
(45) Date of Patent: Oct. 9, 2018

(54) BLOCKADE OF RGMB FOR REDUCING TRANSPLANTATION-ASSOCIATED IMMUNE RESPONSES

(71) Applicant: The Board of Trustees of the Leland Stanford Junior University, Stanford, CA (US)

(72) Inventors: Everett Hurteau Meyer, Reston, VA (US); Rosemarie H. Dekruyff, Portola Valley, CA (US); Panagiota Iliopoulou, San Carlos, CA (US); Yuchiao Hsu, Palo Alto, CA (US); Magdiel Perez Cruz, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/343,085

(22) Filed: Nov. 3, 2016

(65) Prior Publication Data

US 2017/0121404 A1    May 4, 2017

Related U.S. Application Data

(60) Provisional application No. 62/250,411, filed on Nov. 3, 2015.

(51) Int. Cl.
| | | |
|---|---|---|
| *C07K 16/28* | (2006.01) | |
| *A61K 39/395* | (2006.01) | |
| *A61K 45/06* | (2006.01) | |
| *C07K 16/22* | (2006.01) | |
| *A61K 39/00* | (2006.01) | |

(52) U.S. Cl.
CPC .......... *C07K 16/28* (2013.01); *A61K 39/3955* (2013.01); *A61K 45/06* (2013.01); *C07K 16/22* (2013.01); *A61K 2039/505* (2013.01); *A61K 2039/545* (2013.01); *C07K 2317/76* (2013.01)

(58) Field of Classification Search
None
See application file for complete search history.

(56) References Cited

PUBLICATIONS

Latchman et al. PD-L2 is a second ligand for PD-1 and inhibits T cell activation, Nature Immunol. 2, 261-268, 2001 (Year: 2001).*
Topalian et al. Immune check point blockade: A common denominator approach. Cancer Cell, 27, 450-461, 2015. (Year: 2015).*
Ito et al. Analysis of the role of negative T cell costimulatory pathways in CD4 and CD8 T cell-mediated alloimmune responses in vivo. J. Immunol. 174, 6648-6656, 2005. (Year: 2005).*
Severyn et al., "Molecular biology, genetics and biochemistry of the repulsive guidance molecule family", Biochemical Journal, Sep. 15, 2009, pp. 393-403, 422(3), Biochemical Society, London, United Kingdom.
Xiao et al., "RGMb is a novel binding partner for PD-L2 and its engagement with PD-L2 promotes respiratory tolerance", J. Exp. Med., Apr. 21, 2014, pp. 943-959, 211(5), The Rockefeller University Press, Birmingham, Alabama.
Metzger et al., "Gene expression of the repulsive guidance molecules during development of the mouse intestine", Dev. Dyn., Jul. 19 2005, pp. 169-175, 234(1), Wiley-Liss, Inc., Hoboken, New Jersey.

* cited by examiner

*Primary Examiner* — Elly-Gerald Stoica
(74) *Attorney, Agent, or Firm* — Pamela J. Sherwood; Bozicevic, Field & Francis LLP

(57) ABSTRACT

RGMb antagonists reduce undesirable immune responses associated with tissue or organ transplantation.

9 Claims, 2 Drawing Sheets
(2 of 2 Drawing Sheet(s) Filed in Color)

BLOCKADE OF RGMB FOR REDUCING TRANSPLANTATION-ASSOCIATED IMMUNE RESPONSES

CROSS REFERENCE

This application claims benefit of U.S. Provisional Patent Application No. 62/250,411, filed Nov. 3, 2015, which application is incorporated herein by reference in its entirety.

BACKGROUND OF THE INVENTION

Transplantation is the act of transferring cells, tissues, or organs from one site to another. The malfunction of an organ system may be corrected with transplantation of an organ (e.g., kidney, liver, heart, lung, or pancreas) from a donor. However, the immune system remains a most formidable barrier to transplantation as a routine medical treatment. The immune system has developed elaborate and effective mechanisms to combat foreign agents. These mechanisms are also involved in the rejection of transplanted organs, which are recognized as foreign by the recipient's immune system.

Understanding these mechanisms is important, as it aids in understanding the clinical features of rejection and, hence, in making an early diagnosis and delivering appropriate treatment. Knowledge of these mechanisms is also critical in developing strategies to minimize rejection and in developing new drugs and treatments that blunt the effects of the immune system on transplanted organs, thereby ensuring longer survival of these organs.

The degree of immune response to a graft depends partly on the degree of genetic disparity between the grafted organ and the host. Xenografts, which are grafts between members of different species, have the most disparity and elicit the maximal immune response, undergoing rapid rejection. Autografts, which are grafts from one part of the body to another (e.g., skin grafts), are not foreign tissue and, therefore, do not elicit rejection. Isografts, which are grafts between genetically identical individuals (e.g., monozygotic twins), also undergo no rejection. Allografts are grafts between members of the same species that differ genetically. This is the most common form of transplantation. The degree to which allografts undergo rejection depends partly on the degree of similarity or histocompatibility between the donor and the recipient.

The degree and type of response also vary with the type of the transplant. Some sites, such as the eye and the brain, are immunologically privileged. Skin grafts are not initially vascularized and so may not manifest rejection until the blood supply develops. The heart, kidneys, and liver are highly vascular organs and can lead to a vigorous cell mediated response in the host.

One of the more common transplantations relates to blood stem cells, particularly allogeneic stem cell transplants, for example in the treatment of cancer, and which have promise for the treatment of blood diseases such as sickle cell anemia, thalassemias, and the like. In an allogeneic transplant, stem cells are collected from a matching donor and transplanted into the patient to suppress the disease and restore the patient's immune system. An allogeneic stem cell transplant is different from an autologous stem cell transplant, which uses stem cells from the patient's own body. Donor cells may be circulating stem/progenitor cells; mobilized peripheral blood, cord blood, etc. Before an allogeneic stem cell transplant, patients are typically treated with intensive high-dose chemotherapy, or a combination of high-dose chemotherapy and radiation therapy. Because immune cells are transferred in the process, however there can be a risk of graft-versus-host-disease (GVHD), a condition where the donated cells attack recipient tissues.

Included in the field of solid organ transplants is the transplantation of pancreatic islet cells. While significant progress has been made, many obstacles remain that preclude its widespread application. An important limitation are the currently inadequate means for preventing islet rejection. Current immunosuppressive regimens are capable of preventing islet failure for months to years, but the agents used in these treatments are expensive and can increase the risk for specific malignancies and opportunistic infections. Further, calcineurin inhibitory immunosuppressive agents such as cyclosporine, FK-506, rapamycin, etc. are known to impair normal islet function and/or insulin action. Of particular concern is the harmful effect of certain widely employed immunosuppressive agents on renal function. For a patient with diabetes, renal function is a crucial factor in determining long-term outcome, and calcineurin inhibitors show significant nephrotoxicity. For diabetic patients, even those with long-standing and difficult-to-control disease, the prognosis for survival can be comparatively much better treating with insulin vs. transplantation. While most islet recipients achieve better glycemia control and suffer less serious hypoglycemia, islet transplantation currently continues to fall short of the definitive diabetes cure.

Improved methods of improving patient health following transplantation is of great interest, including providing efficient therapeutic strategies targeting GVHD, with lower side effects.

PUBLICATIONS

Severyn C J, Shinde U, Rotwein P. Molecular biology, genetics and biochemistry of the repulsive guidance molecule family. *Biochem. J.* 2009; 422(3):393-403.

Xiao Y, Yu S, Zhu B, et al. RGMb is a novel binding partner for PD-L2 and its engagement with PD-L2 promotes respiratory tolerance. *J. Exp. Med.* 2014; 211(5):943-959.

Metzger M, Conrad S, Alvarez-Bolado G, Skutella T, Just L. Gene expression of the repulsive guidance molecules during development of the mouse intestine. *Dev. Dyn.* 2005; 234(1):169-175.

SUMMARY OF THE INVENTION

Compositions and methods are provided for reducing undesirable immune responses associated with tissue transplantation, including transplantation of hematopoietic cells, solid tissues, organs, pancreatic islet cells, and the like. In the methods of the invention, an antagonist of RGMb is administered to a transplant recipient in a dose effective to reduce undesirable immune responses. In some embodiments the undesirable immune response is activity by donor lymphocytes in graft versus host disease (GVHD). In some embodiments the undesirable immune response is inflammation leading to loss of function of transplanted pancreatic islets. It is shown herein that blockade of RGMb with an antagonistic antibody protects against GVHD and loss of transplanted islet function, e.g. reducing islet allograft transplant rejection and preserving islet metabolic function during inflammation. The methods provided herein include, in some cases, following transplantation of an HLA-matched or HLA-mismatched solid organ, with administration of an RGMb antagonist to a recipient.

The present invention relates to blockade of Repulsive Guidance Molecule (RGMb, Dragon), which is one of the three repulsive guidance molecule (RGM) family members, and is a glycophosphatidylinositol-anchored membrane proteins. RGMb is a bone morphogenetic protein (BMP) coreceptor and sensitizer of BMP signaling. It has also been reported that RGMb interacts with programmed death ligand 2 (PD-L2), a known ligand of PD-1. PD-L2 and BMP-2/4 bind to distinct sites on RGMb.

In some embodiments blockade of RGMb is achieved by contacting cells with an antagonist of RGMb. In some the antagonist is a polypeptide, including without limitation an antibody. In other embodiments blockade is achieved with a polynucleotide, e.g. an anti-sense oligonucleotide, an RNAi, and the like. In some embodiments the antibody is human or humanized, e.g. for treatment of a human patient. Antibodies may be selected for low activation through the Fc receptor; or may be selected to be active in ADCC or ADCP. In some embodiments the antibody is a bivalent antibody. In some embodiments the antibody interferes with signaling mediated by RGMb.

In some embodiments the transplantation is a hematopoietic cell transplantation, e.g. stem cell, progenitor cell, etc. In some such embodiments a patient is treated for prevention or treatment of GVHD. In some embodiments the GVHD is acute GVHD. In some embodiments the GVHD is chronic GVHD. In some embodiments the transplant recipient is subjected to myeloablative, reduced intensity or non-myeloblative conditioning prior to transplantation and treatment with an antagonist of RBMB. The therapeutic methods of the invention promote immune tolerance and better immunity in the hematopoietic transplant setting.

In some embodiments the transplantation is a solid tissue transplantation, including organs and fragments thereof. In some cases, the solid organ is HLA-matched or HLA-mismatched. In some cases, the solid organ is selected from a group consisting of a heart, intestine, liver, lung, pancreas and kidney. The solid organ may be a portion of a whole organ, may be obtained from a living donor or a deceased donor and/or may be related or non-related to the recipient. In some embodiments the solid tissue is pancreatic tissue. In some embodiments the pancreatic tissue comprises islets of Langerhans, which are optionally purified from other pancreatic tissue. The islets or cells derived therefrom usually comprise beta cells.

In some cases, treatment is administered after determining whether a donor and a recipient are HLA-matched or HLA-mismatched by typing HLA alleles HLA-A, HLA-B and HLA-DR in the donor and the recipient. HLA-matched may refer to a match wherein each of the HLA alleles at HLA-A, HLA-B and HLA-DR are the same between the donor and the recipient. HLA-mismatched may refer to a match wherein at least one HLA allele at HLA-A, HLA-B and HLA-DR is different between the donor and the recipient.

In some embodiments, an effective dose of a RGMb antagonist is administered to a transplant recipient. In some embodiments the administering is performed prior to transplantation. In some embodiments the administering is performed following transplantation, e.g. substantially simultaneously, after about 1 day, after about 2 days, after about 3 days, after about 4 days, after about 5 days, after about 6 days, after about one week, after about 2 weeks, after about 3 week, after about 4 weeks, or more. In some embodiment, administering to a transplant recipient is performed in combination with ex vivo treatment of the graft with an effective dose of an RGMb antagonist.

In some embodiments, the invention provides an RGMb antagonist, e.g. an antibody that specifically binds to RGMb and blocks activity, as well as pharmaceutical formulations of the same. In another aspect, the invention provides pharmaceutical formulations containing one or more RGMb antagonist(s) and a pharmaceutically acceptable carrier. The formulation may comprise one or more active agents or a mixture or "cocktail" of agents having different activities, e.g. including one or more additional immunosuppressive agents. The formulation may be provided in a unit dose, e.g. an effective dose of an agonist in a sterile container suitable for clinical use.

Also disclosed herein are kits for organ transplantation. The kits provided herein describe, in some cases, a composition of an RGMb antagonist which may be administered to a recipient following transplantation of an HLA-matched or HLA-mismatched solid organ, organ tissue, or hematopoietic cells.

These and other aspects and embodiments of the invention are described in more detail below.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE EMBODIMENTS

Definitions

Figure 1:
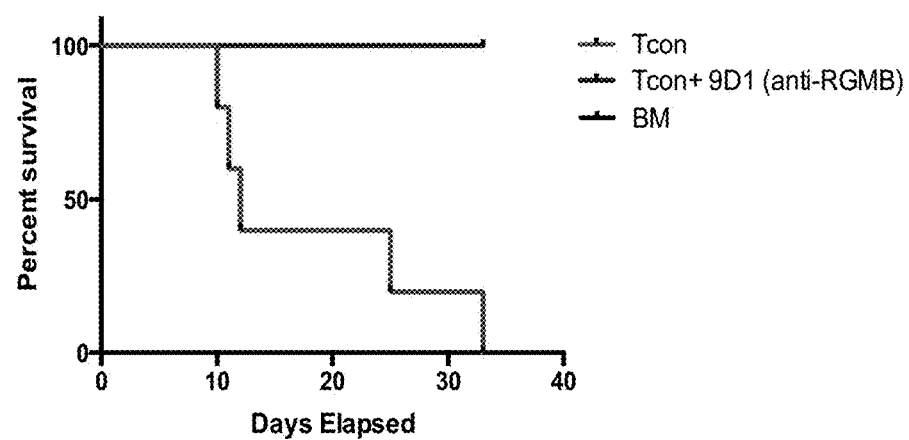
FIG. 1. Blockade of RGMb with an antagonistic rat anti-mouse mAb 9D1 prevents GVHD in the a mouse. 9D1 was dosed on day −1, +1, +5, +9, +15 and treated mice survived better than isotype controls (replicated in 2 experiments, n=5 mice per group, Kaplan Meier survival analysis p=0.01.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

General methods in molecular and cellular biochemistry can be found in such standard textbooks as Molecular Cloning: A Laboratory Manual, 3rd Ed. (Sambrook et al., CSH Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

As used herein, the term "prevention" refers to alleviating the disease or condition from occurring in a subject which has not yet been diagnosed as having it. As used herein, the term "subject" denotes a mammal, such as a rodent, a feline, a canine, and a primate. Preferably a subject according to the invention is a human.

The terms "individual," "subject," "host," and "patient," are used interchangeably herein and refer to any mammalian subject for whom diagnosis, treatment, or therapy is desired, particularly humans.

The term "subject" includes mammals, e.g. cats, dogs, horses, pigs, cows, sheep, rodents, rabbits, squirrels, bears, primates such as chimpanzees, gorillas, and humans.

As used herein, the term "solid organ transplantation" is used in accordance with the conventional meaning of the term, where an organ from a donor, which donor may be living or deceased, in placed into the body of a recipient in the appropriate position and cardiovascular connections to be physiologically integrated into the recipient. Transplantation of pancreatic tissue, e.g. pancreatic islets comprising beta cells, is of particular interest for the methods of the invention, as is the transplantation of hematopoietic cells, e.g. in stem and/or progenitor cell transplantation, although the methods do not exclude transplantation of other organs, e.g. including kidney, pancreatic islet cells; heart; intestine, liver; lung, skin, and the like as known in the art. In some embodiments the transplantation involves multiple anastomoses, e.g. transplantation of lung, heart, liver, kidney. The transplanted organ may be referenced as a "graft", and the physiological integration of the organ may be referred to as engraftment.

The term "graft management" refers to therapeutic methods that induce and/or promote repair engraftment of a solid organ, but not limited to, islet cell transplantation.

RGMb.

Repulsive guidance molecules (RGMs) compose a family of glycosylphosphatidylinositol (GPI)-anchored axon guidance molecules and perform several functions during neural development. Dragon (RGMb) is a member of the family which is expressed early in the developing nervous system. Bone morphogenetic proteins (BMPs) are members of the transforming growth factor (TGF)beta superfamily of ligands that regulate many crucial aspects of embryonic development and organogenesis. DRAGON enhances BMP but not TGFbeta signaling. DRAGON binds directly to BMP2 and BMP4 but not to BMP7 or other TGFbeta ligands. The enhancing action of DRAGON on BMP signaling is also reduced by administration of Noggin, a soluble BMP antagonist, indicating that the action of DRAGON is ligand-dependent. DRAGON associates directly with BMP type I (ALK2, ALK3, and ALK6) and type II (ActRII and ActRIIB) receptors, and its signaling is reduced by dominant negative Smad1 and ALK3 or -6 receptors. In the *Xenopus* embryo, DRAGON both reduces the threshold of the ability of Smad1 to induce mesodermal and endodermal markers and alters neuronal and neural crest patterning. The direct interaction of DRAGON with BMP ligands and receptors indicates that it is a BMP co-receptor that potentiates BMP signaling. Programmed death ligand 2 (PD-L2), a known ligand of PD-1, also binds to RGMb. PD-L2 and BMP-2/4 bind to distinct sites on RGMb.

The genetic sequence of human RGMb may be accessed at Genbank, NM_001012761, see Samad et al. (2004) J. Neurosci. 24 (8), 2027-2036 and Samad et al. (2005) J. Biol. Chem. 280 (14), 14122-14129, each herein specifically incorporated by reference.

By RGMb inhibitory agent or antagonist is meant an agent that inhibits the activity, e.g. binding to; interfering with binding partners; reducing expression; reducing signaling; etc. The inhibitory agent may inhibit the activity by a variety of different mechanisms. In certain embodiments, the inhibitory agent is one that binds to RGMb and, in doing so, inhibits its activity.

Representative RGMb inhibitory agents include, but are not limited to: antisense oligonucleotides, and the like. Other agents of interest include, but are not limited to: antibodies, naturally occurring or synthetic small molecule compounds of interest, which include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing appropriate screening protocols.

The antisense reagent may be antisense oligonucleotides (ODN), particularly synthetic ODN having chemical modifications from native nucleic acids, or nucleic acid constructs that express such antisense molecules as RNA. The antisense sequence is complementary to RGMb, and inhibits its expression. One or a combination of antisense molecules may be administered, where a combination may comprise multiple different sequences.

Antisense molecules may be produced by expression of all or a part of the target RGMb sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 25, usually not more than about 23-22 nucleotides in length, where the length is governed by efficiency of inhibition, specificity, including absence of cross-reactivity, and the like.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature that alter the chemistry of the backbone, sugars or heterocyclic bases.

Anti-sense molecules of interest include antagomir RNAs, e.g. as described by Krutzfeldt et al., herein specifically incorporated by reference. Small interfering double-stranded RNAs (siRNAs) engineered with certain 'drug-like' properties such as chemical modifications for stability and cholesterol conjugation for delivery have been shown to achieve therapeutic silencing of an endogenous gene in vivo. To develop a pharmacological approach for silencing RGMbs in vivo, chemically modified, cholesterol-conjugated single-stranded RNA analogues complementary to RGMb mRNA sequences are developed, termed 'antagomirs'. Antagomir RNAs may be synthesized using standard solid phase oligonucleotide synthesis protocols. The RNAs are conjugated to cholesterol, and may further have a phosphorothioate backbone at one or more positions.

Also of interest in certain embodiments are RNAi agents. In representative embodiments, the RNAi agent targets the precursor molecule of the RGMb mRNA sequence. By RNAi agent is meant an agent that modulates expression by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

In certain embodiments, instead of the RNAi agent being an interfering ribonucleic acid, e.g., an siRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

An antagonist may particularly include antibodies that selectively bind to RGMb and inhibit, or block activity. Antibodies specific for human RGMb include, for example, the rat anti-human antibody BFH-5C9; mouse anti-human antibody (Clone 398528); etc., or antibodies can be generated using art-recognized techniques.

Antibodies, also referred to as immunoglobulins, conventionally comprise at least one heavy chain and one light, where the amino terminal domain of the heavy and light chains is variable in sequence, hence is commonly referred to as a variable region domain, or a variable heavy (VH) or variable light (VH) domain. The two domains conventionally associate to form a specific binding region, although specific binding can also be obtained with heavy chain only variable sequences, and a variety of non-natural configurations of antibodies are known and used in the art.

A "functional" or "biologically active" antibody or antigen-binding molecule is one capable of exerting one or more of its natural activities in structural, regulatory, biochemical or biophysical events. For example, a functional antibody may have the ability to specifically bind an antigen and the binding may in turn elicit or alter a cellular or molecular event such as signaling transduction or enzymatic activity. A functional antibody may also block ligand activation of a receptor or act as an agonist or antagonist.

The term "antibody" herein is used in the broadest sense and specifically covers monoclonal antibodies, polyclonal antibodies, monomers, dimers, multimers, multispecific antibodies (e.g., bispecific antibodies), heavy chain only antibodies, three chain antibodies, single chain Fv, nanobodies, etc., and also include antibody fragments, so long as they exhibit the desired biological activity (Miller et al (2003) Jour. of Immunology 170:4854-4861). Antibodies may be murine, human, humanized, chimeric, or derived from other species.

The term antibody may reference a full-length heavy chain, a full length light chain, an intact immunoglobulin molecule; or an immunologically active portion of any of these polypeptides, i.e., a polypeptide that comprises an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule, including engineered subclasses with altered Fc portions that provide for reduced or enhanced effector cell activity. The immunoglobulins can be derived from any species. In one aspect, the immunoglobulin is of largely human origin.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method.

The antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape etc.) and human constant region sequences.

An "intact antibody chain" as used herein is one comprising a full length variable region and a full length constant region. An intact "conventional" antibody comprises an intact light chain and an intact heavy chain, as well as a light chain constant domain (CL) and heavy chain constant domains, CH1, hinge, CH2 and CH3 for secreted IgG. Other isotypes, such as IgM or IgA may have different CH domains. The constant domains may be native sequence constant domains (e.g., human native sequence constant domains) or amino acid sequence variants thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors. Constant region variants include those that alter the effector profile, binding to Fc receptors, and the like.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known. Ig forms include hinge-modifications or hingeless forms (Roux et al (1998) J. Immunol. 161:4083-4090; Lund et al (2000) Eur. J. Biochem. 267: 7246-7256; US 2005/0048572; US 2004/0229310). The light chains of antibodies from any vertebrate species can be assigned to one of two clearly distinct types, called K and $\lambda$, based on the amino acid sequences of their constant domains.

A "functional Fc region" possesses an "effector function" of a native-sequence Fc region. Exemplary effector functions include C1q binding; CDC; Fc-receptor binding; ADCC; ADCP; down-regulation of cell-surface receptors (e.g., B-cell receptor), etc. Such effector functions generally require the Fc region to be interact with a receptor, e.g. the Fc$\gamma$RI; Fc$\gamma$RIIA; Fc$\gamma$RIIB1; Fc$\gamma$RIIB2; Fc$\gamma$RIIIA; Fc$\gamma$RIIIB receptors, and the law affinity FcRn receptor; and can be assessed using various assays as disclosed, for example, in definitions herein. A "dead" Fc is one that has been mutagenized to retain activity with respect to, for example, prolonging serum half-life, but which does not activate a high affinity Fc receptor.

A "native-sequence Fc region" comprises an amino acid sequence identical to the amino acid sequence of an Fc region found in nature. Native-sequence human Fc regions include a native-sequence human IgG1 Fc region (non-A and A allotypes); native-sequence human IgG2 Fc region; native-sequence human IgG3 Fc region; and native-sequence human IgG4 Fc region, as well as naturally occurring variants thereof.

A "variant Fc region" comprises an amino acid sequence that differs from that of a native-sequence Fc region by virtue of at least one amino acid modification, preferably one or more amino acid substitution(s). Preferably, the variant Fc region has at least one amino acid substitution compared to a native-sequence Fc region or to the Fc region of a parent polypeptide, e.g., from about one to about ten amino acid substitutions, and preferably from about one to about five amino acid substitutions in a native-sequence Fc region or in the Fc region of the parent polypeptide. The variant Fc region herein will preferably possess at least about 80% homology with a native-sequence Fc region and/or with an Fc region of a parent polypeptide, and most preferably at least about 90% homology therewith, more preferably at least about 95% homology therewith.

Variant Fc sequences may include three amino acid substitutions in the CH2 region to reduce Fc$\gamma$RI binding at EU index positions 234, 235, and 237 (see Duncan et al., (1988) Nature 332:563). Two amino acid substitutions in the complement C1q binding site at EU index positions 330 and 331 reduce complement fixation (see Tao et al., J. Exp. Med. 178:661 (1993) and Canfield and Morrison, J. Exp. Med. 173:1483 (1991)). Substitution into human IgG1 of IgG2 residues at positions 233-236 and IgG4 residues at positions 327, 330 and 331 greatly reduces ADCC and CDC (see, for example, Armour K L. et al., 1999 Eur J Immunol. 29(8): 2613-24; and Shields R L. et al., 2001. J Biol Chem. 276(9):6591-604). Other Fc variants are possible, including without limitation one in which a region capable of forming a disulfide bond is deleted, or in which certain amino acid residues are eliminated at the N-terminal end of a native Fc form or a methionine residue is added thereto. Thus, in one embodiment of the invention, one or more Fc portions of the scFc molecule can comprise one or more mutations in the hinge region to eliminate disulfide bonding. In yet another embodiment, the hinge region of an Fc can be removed entirely. In still another embodiment, the molecule can comprise an Fc variant.

Further, an Fc variant can be constructed to remove or substantially reduce effector functions by substituting, deleting or adding amino acid residues to effect complement binding or Fc receptor binding. For example, and not limitation, a deletion may occur in a complement-binding site, such as a C1q-binding site. Techniques of preparing such sequence derivatives of the immunoglobulin Fc fragment are disclosed in International Patent Publication Nos. WO 97/34631 and WO 96/32478. In addition, the Fc domain may be modified by phosphorylation, sulfation, acylation, glycosylation, methylation, farnesylation, acetylation, amidation, and the like.

The Fc may be in the form of having native sugar chains, increased sugar chains compared to a native form or decreased sugar chains compared to the native form, or may be in an aglycosylated or deglycosylated form. The increase, decrease, removal or other modification of the sugar chains may be achieved by methods common in the art, such as a chemical method, an enzymatic method or by expressing it in a genetically engineered production cell line. Such cell lines can include microorganisms, e.g. *Pichia Pastoris*, and mammalians cell line, e.g. CHO cells, that naturally express glycosylating enzymes. Further, microorganisms or cells can be engineered to express glycosylating enzymes, or can be rendered unable to express glycosylation enzymes (See e.g., Hamilton, et al., Science, 313:1441 (2006); Kanda, et al, J. Biotechnology, 130:300 (2007); Kitagawa, et al., J. Biol. Chem., 269 (27): 17872 (1994); Ujita-Lee et al., J. Biol. Chem., 264 (23): 13848 (1989); Imai-Nishiya, et al, BMC Biotechnology 7:84 (2007); and WO 07/055916). As one example of a cell engineered to have altered sialylation activity, the alpha-2,6-sialyltransferase 1 gene has been engineered into Chinese Hamster Ovary cells and into sf9 cells. Antibodies expressed by these engineered cells are thus sialylated by the exogenous gene product. A further method for obtaining Fc molecules having a modified amount of sugar residues compared to a plurality of native molecules includes separating said plurality of molecules into glycosylated and non-glycosylated fractions, for example, using lectin affinity chromatography (See e.g., WO 07/117505). The presence of particular glycosylation moieties has been shown to alter the function of Immunoglobulins. For example, the removal of sugar chains from an Fc molecule results in a sharp decrease in binding affinity to the C1q part of the first complement component C1 and a decrease or loss in antibody-dependent cell-mediated cytotoxicity (ADCC) or complement-dependent cytotoxicity (CDC), thereby not inducing unnecessary immune responses in vivo. Additional important modifications include sialylation and fucosylation: the presence of sialic acid in IgG has been correlated with anti-inflammatory activity (See e.g., Kaneko, et al, Science 313:760 (2006)), whereas removal of fucose from the IgG leads to enhanced ADCC activity (See e.g., Shoj-Hosaka, et al, J. Biochem., 140:777 (2006)).

In alternative embodiments, antibodies may have an Fc sequence with enhanced effector functions, e.g. by increasing their binding capacities to FcγRIIIA and increasing ADCC activity. For example, fucose attached to the N-linked glycan at Asn-297 of Fc sterically hinders the interaction of Fc with FcγRIIIA, and removal of fucose by glyco-engineering can increase the binding to FcγRIIIA, which translates into >50-fold higher ADCC activity compared with wild type IgG1 controls. Protein engineering, through amino acid mutations in the Fc portion of IgG1, has generated multiple variants that increase the affinity of Fc binding to FcγRIIIA. Notably, the triple alanine mutant S298A/E333A/K334A displays 2-fold increase binding to FcγRIIIA and ADCC function. S239D/I332E (2×) and S239D/I332E/A330L (3×) variants have a significant increase in binding affinity to FcγRIIIA and augmentation of ADCC capacity in vitro and in vivo. Other Fc variants identified by yeast display also showed the improved binding to FcγRIIIA and enhanced tumor cell killing in mouse xenograft models. See, for example Liu et al. (2014) JBC 289(6):3571-90, herein specifically incorporated by reference.

The term "Fc-region-comprising antibody" refers to an antibody that comprises an Fc region. The C-terminal lysine (residue 447 according to the EU numbering system) of the Fc region may be removed, for example, during purification of the antibody or by recombinant engineering the nucleic acid encoding the antibody. Accordingly, an antibody having an Fc region according to this invention can comprise an antibody with or without K447.

"Humanized" forms of non-human (e.g., rodent) antibodies, including single chain antibodies, are chimeric antibodies (including single chain antibodies) that contain minimal sequence derived from non-human immunoglobulin. See, for example, Jones et al, (1986) Nature 321:522-525; Chothia et al (1989) Nature 342:877; Riechmann et al (1992) J. Mol. Biol. 224, 487-499; Foote and Winter, (1992) J. Mol. Biol. 224:487-499; Presta et al (1993) J. Immunol. 151, 2623-2632; Werther et al (1996) J. Immunol. Methods 157:4986-4995; and Presta et al (2001) Thromb. Haemost. 85:379-389. For further details, see U.S. Pat. Nos. 5,225,539; 6,548,640; 6,982,321; 5,585,089; 5,693,761; 6,407,213; Jones et al (1986) Nature, 321:522-525; and Riechmann et al (1988) Nature 332:323-329.

As used herein, a "recipient" is an individual to whom an organ, tissue or cells from another individual (donor), commonly of the same species, has been transferred. For the purposes of the present disclosure, a recipient and a donor are either HLA-matched or HLA-mismatched.

As used herein, the term "solid organ transplantation" is used in accordance with the conventional meaning of the term, where an organ from a donor, which donor may be living or deceased, in placed into the body of a recipient in the appropriate position and cardiovascular connections to be physiologically integrated into the recipient. Transplantation of a pancreatic islets is of particular interest for the methods of the disclosure, although the methods do not exclude transplantation of other organs, e.g. kidney; heart; lungs, intestine, liver, and the like as known in the art. The transplanted organ may be referenced as a "graft", and the physiological integration of the organ may be referred to as engraftment.

Solid organs may be transplanted from a donor to a recipient such that the organ is placed into the appropriate position in the recipient body. In some cases, the cardiovascular connections between the solid organ may be physiologically integrated into the recipient body. In some cases, the organ may be from a living donor. In other cases, the organ may be from a deceased donor. In some cases, the solid organ may be HLA-matched between the donor and the recipient. In other cases, the solid organ may be HLA-mismatched between the donor and the recipient.

Any solid organ that may be used for organ transplantation may be used with the methods described herein. In some cases, the organ may be a kidney, lung, pancreas, pancreatic islet cells, heart, intestine, colon, liver, skin, muscle, gum, eye, tooth and the like as known to those of skill in the art. In some cases, the organ may be a complete organ. In other cases, the organ may be a portion of an organ. In other cases, the organ may be cells from a tissue of an organ. Using the methods described herein, the solid organ is harvested and transplanted in accordance with conventional practice.

Hematopoietic stem cell transplantation (HCT) is the transplantation of multipotent hematopoietic stem cells, usually derived from bone marrow, peripheral blood, or umbilical cord blood. Where the donor is deceased, hematopoietic cells may be obtained from bone marrow (e.g. vertebrae, pelvic bone, etc). Where the donor is a living donor, hematopoietic cells may be mobilized (e.g. with G-CSF), and collected by apheresis or similar methods. Alternatively, cells may be obtained from bone marrow (e.g. pelvic bone, etc).

Hematopoietic cells can be frozen (e.g., cryopreserved) for prolonged periods without damaging a significant number of cells. To cryopreserve HSC, a preservative, DMSO, must be added, and the cells must be cooled very slowly in a controlled-rate freezer to prevent osmotic cellular injury during ice crystal formation. HSC may be stored for years in a cryofreezer, which typically uses liquid nitrogen.

A recipient's immune system may be conditioned with a non-myeloablative procedure prior to infusion of the hematopoietic cells. The conditioning regimen can include treatment with anti-thymocyte globulin (ATG); total lymphoid irradiation, and corticosteroids (e.g. prednisone) usually for a period of from about 10 to 12 days (e.g. for about 11 days).

"Major histocompatibility complex antigens" ("MHC", also called "human leukocyte antigens", HLA) are protein molecules expressed on the surface of cells that confer a unique antigenic identity to these cells. MHC/HLA antigens are target molecules that are recognized by T-cells and natural killer (NK) cells as being derived from the same source of hematopoietic stem cells as the immune effector cells ("self") or as being derived from another source of hematopoietic reconstituting cells ("non-self"). Two main classes of HLA antigens are recognized: HLA class I and HLA class II. HLA class I antigens (A, B, and C in humans) render each cell recognizable as "self," whereas HLA class II antigens (DR, DP, and DQ in humans) are involved in reactions between lymphocytes and antigen presenting cells. Both have been implicated in the rejection of transplanted organs.

An important aspect of the HLA gene system is its polymorphism. Each gene, MHC class I (A, B and C) and MHC class II (DP, DQ and DR) exists in different alleles. HLA alleles are designated by numbers and subscripts. For example, two unrelated individuals may carry class I HLA-B, genes B5, and Bw41, respectively. Allelic gene products differ in one or more amino acids in the α and/or β domain(s). Large panels of specific antibodies or nucleic acid reagents are used to type HLA haplotypes of individuals, using leukocytes that express class I and class II molecules. The genes most important for HLA typing are the six MHC Class I and Class II proteins, two alleles for each of HLA-A; HLA-B and HLA-DR.

The HLA genes are clustered in a "super-locus" present on chromosome position 6p21, which encodes the six classical transplantation HLA genes and at least 132 protein coding genes that have important roles in the regulation of the immune system as well as some other fundamental molecular and cellular processes. The complete locus measures roughly 3.6 Mb, with at least 224 gene loci. One effect of this clustering is that "haplotypes", i.e. the set of alleles present on a single chromosome, which is inherited from one parent, tend to be inherited as a group. The set of alleles inherited from each parent forms a haplotype, in which some alleles tend to be associated together. Identifying a patient's haplotypes can help predict the probability of finding matching donors and assist in developing a search strategy, because some alleles and haplotypes are more common than others and they are distributed at different frequencies in different racial and ethnic groups.

As used herein, the term "HLA matched" refers to a donor recipient pair in which none of the HLA antigens are mismatched between the donor and recipient. HLA matched (i.e., where all of the 6 alleles are matched) donor/recipient pairs have a decreased risk of graft v. host disease (GVHD) relative to mismatched pairs (i.e. where at least one of the 6 alleles is mismatched).

As used herein, the term "HLA mismatched" refers to a donor recipient pair in which at least one HLA antigen, in particular with respect to HLA-A, HLA-B and HLA-DR, is mismatched between the donor and recipient. In some cases, one haplotype is matched and the other is mismatched. This situation is frequently found with organs from living or deceased donors. HLA mismatched donor/recipient pairs have an increased risk of GVHD relative to perfectly matched pairs (i.e. where all 6 alleles are matched).

HLA alleles are typically noted with a variety of levels of detail. Most designations begin with HLA- and the locus name, then * and some (even) number of digits specifying the allele. The first two digits specify a group of alleles. Older typing methodologies often could not completely distinguish alleles and so stopped at this level. The third through fourth digits specify a synonymous allele. Digits five through six denote any synonymous mutations within the coding frame of the gene. The seventh and eighth digits distinguish mutations outside the coding region. Letters such as L, N, Q, or S may follow an allele's designation to specify an expression level or other non-genomic data known about it. Thus, a completely described allele may be up to 9 digits long, not including the HLA-prefix and locus notation.

"Immunosuppression", as used herein, refers to the treatment of a graft recipient with agents, primarily to diminish the immune responses of the host immune system against the graft, although the agents may also diminish GVHD of the donor hematopoietic cells. Immunosuppressive treatment of the transplantation patient begins with the induction phase, perioperatively and immediately after transplantation. Maintenance therapy then continues. Induction and maintenance strategies use different medicines at specific doses or at doses adjusted to achieve target therapeutic levels to give the transplantation patient the best hope for long-term graft survival.

Primary immunosuppressive agents include calcineurin inhibitors, which combine with binding proteins to inhibit calcineurin activity, and which include, for example, tacrolimus, cyclosporine A, etc. Levels of both cyclosporine and tacrolimus must be carefully monitored. Initially, levels can be kept in the range of 10-20 ng/mL, but, after 3 months, levels may be kept lower (5-10 ng/mL) to reduce the risk of nephrotoxicity.

Adjuvant agents are usually combined with a calcineurin inhibitor and include steroids, azathioprine, mycophenolate mofetil, and sirolimus. Protocols of interest include a calcineurin inhibitor with mycophenolate mofetil. The use of adjuvant agents allows clinicians to achieve adequate immunosuppression while decreasing the dose and toxicity of individual agents. Mycophenolate mofetil in kidney transplant recipients has assumed an important role in immunosuppression after several clinical trials have shown a markedly decreased prevalence of acute cellular rejection compared with azathioprine and a reduction in 1-year treatment failures.

Antibody-based therapy uses monoclonal (e.g., muromonab-CD3) or polyclonal antibodies or anti-CD25 antibodies (e.g., basiliximab, daclizumab) and is administered in the early posttransplant period (up to 8 wk). Antibody-based therapy allows for avoidance or dose reduction of calcineurin inhibitors, possibly reducing the risk of nephrotoxicity. The adverse effect profile of the polyclonal and monoclonal antibodies limits their use in some patients.

"Acute transplant rejection" is the rejection by the immune system of a transplanted organ. Acute rejection is characterized by infiltration of the transplanted tissue by immune cells of the recipient, which carry out their effector function and destroy the transplanted tissue. The onset of acute rejection is rapid and generally occurs in humans within a few weeks after transplant surgery.

Generally, acute rejection is inhibited or suppressed with immunosuppressive drugs. Steroids are the mainstay of therapy for acute rejection episodes. The typical dosage is 3-5 mg/kg/d for 3-5 days, which is then tapered to a maintenance dose. ATG and muromonab-CD3 also find use.

"Chronic transplant rejection" generally occurs in humans within several months to years after engraftment, even in the presence of successful immunosuppression of acute rejection. Fibrosis is a common factor in chronic rejection of all types of organ transplants. Chronic rejection can typically be described by a range of specific disorders that are characteristic of the particular organ. For example, in lung transplants, such disorders include fibroproliferative destruction of the airway (bronchiolitis obliterans); in heart transplants or transplants of cardiac tissue, such as valve replacements, such disorders include fibrotic atherosclerosis; in kidney transplants, such disorders include, obstructive nephropathy, nephrosclerorsis, tubulointerstitial nephropathy; and in liver transplants, such disorders include disappearing bile duct syndrome.

Chronic rejection can also be characterized by ischemic insult, denervation of the transplanted tissue, hyperlipidemia and hypertension associated with immunosuppressive drugs. Unless inadequate immunosuppression is the cause of rejection, changes in immunosuppressive therapy are generally not effective in reversing chronic rejection. Control of blood pressure, treatment of hyperlipidemia, and management of diabetes are the current mainstays of treatment for graft preservation.

The term "transplant rejection" encompasses both acute and chronic transplant rejection. In transplant rejection, the transplanted tissue is rejected and destroyed by the recipient's immune system. Acute rejection may occur to some degree in all transplants, except in the cases of identical twins or during immunosuppression. Acute rejection may begin as soon as one week after transplant and greatest risk for development of acute rejection occurs in the first three months following transplant. Chronic rejection is the long-term loss of function of a transplanted organ.

Graft versus Host Disease (GVHD) is a major debilitating and potentially lethal, side effect of bone marrow transplantation. It occurs when lymphocytes from the donor present in the bone marrow inoculums attack and destroy healthy tissues of the recipient.

Acute GVHD occurs in recipients of allogeneic HSC transplants (in 40% of HLA-matched sibling graft recipients and 80% of unrelated donor graft recipients). It causes fever, rash, hepatitis with hyperbilirubinemia, vomiting, diarrhea, abdominal pain (which may progress to ileus), and weight loss. Risk factors include HLA and sex mismatching; unrelated donor; older age of recipient, donor, or both; donor presensitization; and inadequate GVHD prophylaxis. Diagnosis is obvious based on history, physical examination, and liver function test results; conventional treatment is methylprednisolone 2 mg/kg IV once/day, increased to 10 mg/kg if there is no response within 5 days.

Chronic GVHD may occur by itself, develop from acute GVHD, or occur after resolution of acute GVHD. It typically occurs 4 to 7 mo after HSC transplantation (range 2 mo to 2 yr). Chronic GVHD occurs in recipients of allogeneic HSC transplants (in about 35 to 50% of HLA-matched sibling graft recipients and 60 to 70% of unrelated donor graft recipients). It affects primarily the skin (eg, lichenoid rash, scleroderma) and mucous membranes (eg, keratoconjunctivitis sicca, periodontitis, orogenital lichenoid reactions), but it also affects the GI tract and liver. Immunodeficiency is a primary feature; bronchiolitis obliterans similar to that after lung transplantation can also develop. Ultimately, GVHD causes death in 20 to 40% of patients who have it.

Approximately half of patients who survive beyond 100 days after allogeneic HCT develop cGvHD. The common sites of organ involvement include the mouth, eyes, skin, gastrointestinal tract, liver and lungs. Manifestations of cGvHD adversely impact patient quality of life and mortality. The three-year survival rates for patients with newly diagnosed "favorable" and "poor" risk cGvHD are approximately 80% and 40%, respectively. Further, only 50% of patients with cGvHD are able to discontinue immunosuppressive treatment within 5 years after its onset. Chronic immunosuppressive therapy increases post-HCT morbidity and mortality with a direct correlation between dose of post-HCT corticosteroid and non-relapse mortality (NRM;

Prophylactic GVHD therapy is the standard of care following HCT. Common strategies to decrease GVHD include the use of agents that control T cell proliferation and activation including cyclosporine, tacrolimus, sirolimus, mycophenolate mofetil, steroids and posttransplant cyclophosphamide.

The current primary treatment for both acute and chronic GVHD are intravenously administered glucocorticoids, such as methylprednison, although oral steroids such as prednisone are also used. The use of these glucocorticoids is designed to suppress the T-cell-mediated immune onslaught on the host tissues; however, in high doses, this immune-suppression raises the risk of infections and cancer relapse.

Pancreatic Islet transplantation. Pancreatic islets, also called islets of Langerhans, are tiny clusters of cells scattered throughout the pancreas. The pancreas is an organ about the size of a hand located behind the lower part of the stomach. Pancreatic islets contain several types of cells, including beta cells, that produce the hormone insulin. The pancreas also makes enzymes that help the body digest and use food. In pancreatic islet allo-transplantation, islets from the pancreas of a deceased organ donor are purified, processed, and transferred into another person. Pancreatic islet allo-transplantation is currently labeled an experimental procedure. Enzymes are usually used to remove islets from the pancreas of a single donor. Transplant patients typically receive two infusions with an average of 400,000 to 500,000 islets per infusion. Once implanted, the beta cells in these islets begin to make and release insulin. The transplants are often performed by infusing the islets through a catheter into the portal vein of the liver.

Pancreatic islets begin to release insulin soon after transplantation. However, full islet function and new blood vessel growth from the new islets take time. Transplant recipients usually take insulin injections until the islets are fully functional. They may also receive various medications before and after transplantation to promote successful implantation and long-term functioning of the islets. However, the autoimmune response that destroyed transplant recipients' own islets in the first place can happen again and attack the transplanted islets.

The risks of pancreatic islet allo-transplantation include the risks associated with the transplant procedure, particularly bleeding and blood clots. The transplanted islets may not function well or may stop functioning entirely. Other risks are the side effects from the immunosuppressive medications that transplant recipients must take to stop the immune system from rejecting the transplanted islets.

By "comprising" it is meant that the recited elements are required in the composition/method/kit, but other elements may be included to form the composition/method/kit etc. within the scope of the claim.

By "consisting essentially of", it is meant a limitation of the scope of composition or method described to the specified materials or steps that do not materially affect the basic and novel characteristic(s) of the subject invention.

By "consisting of", it is meant the exclusion from the composition, method, or kit of any element, step, or ingredient not specified in the claim.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy may be administered during the symptomatic stage of the disease, and in some cases after the symptomatic stage of the disease.

A "therapeutically effective amount" is intended for an amount of active agent which is necessary to impart therapeutic benefit to a subject. For example, a "therapeutically effective amount" is an amount which induces, ameliorates or otherwise causes an improvement in the pathological symptoms, disease progression or physiological conditions associated with a disease or which improves resistance to a disorder.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer, individuals with autoimmune diseases, with pathogen infections, and the like. Subjects may be human, but also include other mammals, particularly those mammals useful as laboratory models for human disease, e.g. mouse, rat, etc.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

Methods

In accordance with the present invention, a therapeutic composition of an antagonist of RGMb is administered as a therapeutic drug to a subject who has undergone a transplant and/or as a prophylactic drug to a transplant. Transplants, as described above, include organs, tissues, hematopoietic cells, etc.

In some embodiments the transplant comprises hematopoietic cells (bone marrow, peripheral stem cells, hematopoietic stem cells, etc.) and the antagonist is provided to treat or prevent the development of GVHD. One of skill in the art can determine the patients who would potentially benefit from a therapeutic agent that would reduce or prevent the development of GVHD. One of skill in the art can determine the therapeutically effective amount of the composition to be administered to a subject based upon several considerations, such as local effects, pharmacodynamics, absorption, metabolism, method of delivery, age, weight, disease severity and response to the therapy.

A further embodiment is treating, preventing or reducing the risk of developing graft-versus-host-disease by administering RGMb antagonist to the donor tissue or cells prior to transplantation into the recipient. It is envisioned that administering the composition to the donor tissue or cells will attenuate the immune cells in the donor and prevent the development of the immune response that is mounted against the recipient's tissue, thus preventing or attenuating GVHD.

In other embodiments the transplant is a solid tissue or organ, including specifically pancreas and/or pancreatic islets. Treatment may be therapeutic or prophylactic to reduce the rejection of the tissue, and to improve function, e.g. in the presence of inflammation.

The RGMb antagonist composition can also be administered parenterally, which includes, but is not limited to intradermal, subcutaneous, intramuscular, intraperitoneal, intravenous, intraarterial, intramyocardial, transendocardial, transepicardial, intrathecal, and infusion techniques. In addition, the RGMb antagonist can be contacted with the donor tissue or cells ex vivo, prior to transplantation.

In an embodiment of the present invention, the composition is administered in an effective amount to decrease, reduce, inhibit or abrogate GVHD and toxicity related to standard therapy. The amount of antibody in the composition may vary from about 1 ng to about 1 g, more preferably, 0.1 mg to about 100 mg.

Treatment regimens may vary as well, and often depend on the health and age of the patient. Certain types of disease will require more aggressive treatment, while at the same time, certain patients cannot tolerate more taxing regimens. The clinician will be best suited to make such decisions based on the known efficacy and toxicity (if any) of the therapeutic formulations.

In specific embodiments, the composition is given in a single dose or multiple doses. The single dose may be administered daily, or multiple times a day, or multiple times a week, or monthly or multiple times a month. A series of doses may be administered daily, or multiple times a day, weekly, or multiple times a week, or monthly, or multiple times a month.

The improvement is any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of an immune response against the recipient.

An improvement in GHVD or graft survival and function is also any observable or measurable improvement. Thus, one of skill in the art realizes that a treatment may improve the patient or subject's condition, but may not be a complete cure of the disease. In certain aspects, the composition is administered in an effective amount to decrease, reduce, inhibit or abrogate levels of immune response from the donor's cells, tissue and/or organ against the host's tissues. GVHD can be acute or chronic or mild or severe. Improvements in acute symptoms include any of the following, for example, decrease skin rash, decrease diarrhea, increase in liver function, decrease in susceptibility to infection. Improvements in chronic symptoms include, but are not limited to decrease skin rash, decrease dermatitis, decrease hair loss, decrease liver damage, decrease dry eyes and mouth, decrease susceptibility to infections and decrease lung and/or gastrointestinal disorders.

In order to increase the effectiveness of administration of the composition of the present invention, it is desirable to combine these compositions with standard therapy. For example, known immunosuppressant agents can be used in combination with the composition of the present invention. Exemplary agents known to prevent organ rejection are T cell modifiers such as cyclosporine (Neoral™, Sandimmune™), prednisone (Novo Prednisone™, Apo Prednisone™), azathioprine (Imuran™), tacrolimus or FK506 (Prograf™), mycophenolate mofetil (CellCept™), OKT3 (Muromorab CO3™, Orthoclone™), ATGAM™ & Thymoglobulin™ or serine-threonine phosphatase calcineurin (CN) inhibitors. In specific embodiments, the standard or approved treatment of GVHD, which is high doses corticosteroids, primarily high-dose methylprednisolone, is used in combination with the composition of the present invention.

In addition to immunosuppressant other anti-rejection and/or anti-GVHD therapies can be used in combination with the methods of the present invention. For example, therapies for preconditioning and prophylaxis of GVHD include, but are not limited to total body irradiation, total lymphoid irradiation, cytosine arabinoside, L-phenylalanine mustard, cyclophosphamide, etoposide, triethylene thiophosphoramide, antithymocyte globulin, bisulfan, tacrolimus, methylprednisolone, cyclosporin, or methotrexate. Experimental therapies for treatment of GVHD include, but are not limited to cytokine inhibitors/antagonists (e.g., anti-TNFα antibody); IL-1 receptor antagonist; recombinant IL-1 receptor; inhibitors of T-cell activation (e.g., tacrolimus); antimetabolites (e.g., mycophenolate mofetil); anti-CD3 antibody (muromonab, OKT3); anti-CD25 antibody; anti-IL2 receptor monoclonal antibody daclizumab; extracorporeal photopheresis using ex vivo 8-methoxypsoralen; anti-thymocyte globulins (Thymoglobulin™ or ATGAM™); ABX-CBL or CBL-1; or Visilizumab (Nuvion™).

The composition of the present invention may precede, be co-current with and/or follow the other agent(s) by intervals ranging from minutes to weeks. In embodiments where the composition of the present invention, and other agent(s) are applied separately to a cell, tissue or organism, one would generally ensure that a significant period of time did not expire between the time of each delivery, such that the composition and agent(s) would still be able to exert an advantageously combined effect on the cell, tissue or organism.

Various combination regimens of the composition and one or more agents are employed. One of skill in the art is aware that the composition of the present invention and agents can be administered in any order or combination.

A RGMb antagonist, e.g. an antibody that binds to and blocks the activity of RBMB, may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment. To prepare pharmaceutical compositions, an effective amount of the antibody may be dissolved or dispersed in a pharmaceutically acceptable carrier or aqueous medium. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils.

The proper fluidity can be maintained, for example, by the use of a coating, such as lecithin, by the maintenance of the required particle size in the case of dispersion and by the use of surfactants.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization.

Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose.

These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered. In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

The invention will further be illustrated in view of the following figures and example.

Administration

Following transplantation of a solid organ or tissues there can be episodes in which an immune response is mounted against the organ. During such episodes, the transplanted tissue is stressed and may suffer diminished function. The function of the transplanted tissue is improved by administration of an antagonist of RGMb.

Diagnosis of a rejection episode may utilize on clinical data, markers for activation of immune function, markers for tissue damage, and the like. Histological signs include: infiltrating T cells, perhaps accompanied by infiltrating eosinophils, plasma cells, and neutrophils, particularly in telltale ratios, structural compromise of tissue anatomy, varying by tissue type transplanted, and injury to blood vessels. Tissue biopsy is restricted, however, by sampling limitations and risks/complications of the invasive procedure. Cellular magnetic resonance imaging (MRI) of immune cells radiolabeled in vivo may provide noninvasive testing.

The formulations of the present invention may be administered to the affected tissue upon an initial indication of a rejection episode, and may be maintained for a period of time; e.g. about 1 day, 2 days, 3 days, 4 days, 5 days, 6 days, 1 week, 10 days, 2 weeks, 3 weeks, etc. as needed. Administration may be as frequent as needed, e.g. hourly, about 3 to 4 hours, semi-daily, daily, etc.

EXPERIMENTAL

Repulsive guidance molecule b (RGMb) is a surface receptor that was discovered as a repulsive axon guidance cue, which directs embryonic brain development by binding to the cell surface receptor neugenin and surface or soluble bone morphogenetic proteins (BMP; 2 and 4 specifically) Recently, RGMb has been shown to play a significant role in lung mucosal immunity in part because it also binds to program cell death protein 2 (PDL-2) through a binding site disparate from its BMP/neurogenin binding sites. RGMb is expressed in brain, lungs, pancreas, and intestines. RGMb is expressed in the intestinal crypts, which is a primary site of GVHD activity. BMP2 and 4 appear to mediate significant inflammatory signals in mucosal surfaces in concert with RGMb binding, whereas PDL-2 binding appears to promote mucosal tolerance. RGMb may play a role in mucosal tolerance important in the HCT setting for the onset of GVHD.

Blockade of RGMb is shown in FIG. 1 to protect against GVHD and allows or facilitates engraftment. Using a standard mouse model of HCT, in which mice are given leukemic cell lines (A20 and BCL2) concomitant to HCT (n=5 mice per group, in at least 3 independent experiments), the animals are treated with antibodies specific for RGMb, and the ability of the animals to clear A20 and BCL2 without developing GVHD is determined.

RGMb has a number of splice variants in human (7 described) and mouse (3+ described). The tissue-specific expression of these variants in non-neural tissues has not been described. mRNA is extracted from murine and human gut, blood and neural tissue sources obtained from our own biobank or the Stanford Cancer Institute biobank. The RGMb locus is amplified, followed by size selection and confirmatory Sanger sequencing using public primers to determine the tissue specific expression of splice variants.

BALB/c recipient mice were treated with lethal total body irradiation consisting of 2 doses of 4.0 Gy administered 4 hours apart. On the same day, $5 \times 10^6$ TCD-BM (T-cell depleted bone marrow) cells were injected via tail vein together with $10^6$ Tcons (conventional T cells) from C57BL/6 mice. One day prior to bone marrow transplantation as well as on days 3, 7 mice received the anti-RGMB mAb (9D1) (400 μg/mouse). Survival upon GVHD induction was assessed.

Mice that received allogeneic Tcons and were treated prophylactically with an anti-RGMB mAb are protected from lethal GVHD compared to the mice that received Tcons alone.

Figure 2:
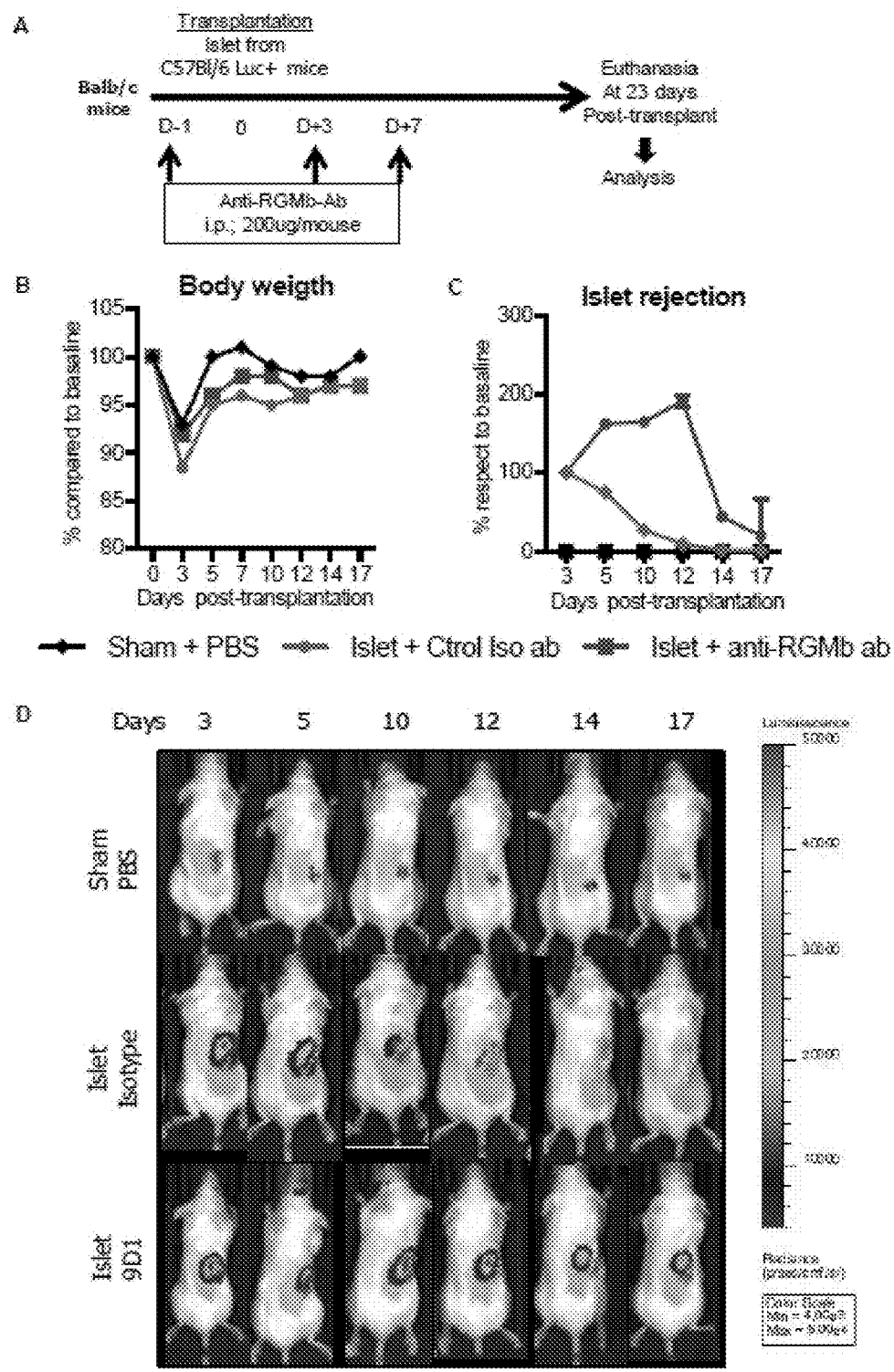
FIG. 2. (A-D) Blockade of RGMB Binding Prolongs Islet Survival and Metabolic Function.

Shown in FIG. 2, C57Bl/6 luc$^+$ (C57Bl/6 luciferase positive) mice were used as pancreas donors. They were sacrificed and pancreatic islets were isolated through perfusion and digestion of the tissue. High quality islets were manually picked and counted. Each female inbred Balb/c mouse received approximately 500 islets. Islets were grafted in a pocket under the left kidney. In vivo imaging was performed with the injection of firefly luciferin prior to image acquisition with an IVIS spectrum imaging system (Xenogen). Images were analyzed with Living Image Software 4.2 (Xenogen).

Blocking RGMb by injection 3 doses of anti-RGMb antibody (clone 9D1) on day-1, +3 and +7 of islet transplantation significant prolonged the islet engraftment compared to the isotype control.

What is claimed is:

1. A method for reducing graft versus host disease following transplantation to a subject, the method comprising:
   administering to said subject a therapeutically effective amount of an antagonistic antibody that specifically binds to Repulsive Guidance Molecule (RGMb), wherein the graft versus host disease is reduced.

2. The method of claim 1, wherein graft cells are contacted with the RGMb antagonistic antibody prior to transplantation.

3. The method of claim 1, wherein the RGMb antagonist is administered following transplantation of the graft.

4. The method of claim 1, wherein the transplantation is transplantation of a solid organ or tissue derived therefrom.

5. The method of claim 4, wherein the organ is pancreas.

6. The method of claim 4, where pancreatic islets are transplanted.

7. A method for reducing graft versus host disease following transplantation of hematopoietic cells to a subject, the method comprising:
   administering to said subject a therapeutically effective amount of an antagonistic antibody that specifically binds to Repulsive Guidance Molecule (RGMb), wherein graft versus host disease is reduced.

8. The method of claim 7, wherein the graft versus host disease is acute graft-versus-host-disease (aGVHD).

9. The method of claim 7, wherein the graft versus host disease is chronic graft-versus-host-disease (cGVHD).

* * * * *